(12) United States Patent
Larsen

(10) Patent No.: US 8,040,236 B2
(45) Date of Patent: Oct. 18, 2011

(54) MEDICATION DELIVERY DEVICE WITH REMINDER UNIT

(75) Inventor: Andre Larsen, Dragor (DK)

(73) Assignee: Novo Nordisk A/S, Bagsvaerd (DK)

( * ) Notice: Subject to any disclaimer, the term of this patent is extended or adjusted under 35 U.S.C. 154(b) by 278 days.

(21) Appl. No.: 11/722,381

(22) PCT Filed: Dec. 27, 2005

(86) PCT No.: PCT/EP2005/014050
§ 371 (c)(1),
(2), (4) Date: Nov. 30, 2009

(87) PCT Pub. No.: WO2006/069778
PCT Pub. Date: Jul. 6, 2006

(65) Prior Publication Data
US 2010/0060464 A1 Mar. 11, 2010

Related U.S. Application Data

(60) Provisional application No. 60/648,778, filed on Feb. 1, 2005.

(30) Foreign Application Priority Data
Dec. 29, 2004 (EP) .................................. 04078558

(51) Int. Cl.
*G08B 1/08* (2006.01)
(52) U.S. Cl. ......... 340/539.12; 340/539.13; 340/309.16; 340/457; 340/573.1; 368/10; 705/2
(58) Field of Classification Search ............. 340/309.16, 340/573.1, 539.1, 539.16, 539.17, 825.49, 340/539.12, 539.13, 539.11, 309.7, 457; 368/10, 1; 700/236; 705/2, 3; 600/300, 301
See application file for complete search history.

(56) References Cited

U.S. PATENT DOCUMENTS

| | | | |
|---|---|---|---|
| 5,805,051 A * | 9/1998 | Herrmann et al. ......... 340/309.4 |
| 6,587,782 B1 * | 7/2003 | Nocek et al. ................. 701/200 |
| 6,650,951 B1 | 11/2003 | Jones et al. |
| 6,744,350 B2 | 6/2004 | Blomquist |
| 6,943,671 B2 * | 9/2005 | McGee et al. ............ 340/384.71 |
| 7,084,758 B1 * | 8/2006 | Cole ........................ 340/539.11 |

(Continued)

FOREIGN PATENT DOCUMENTS

JP 2003-518410 6/2003

(Continued)

OTHER PUBLICATIONS

The International Search Report and Written Opinion dated Dec. 7, 2006.

(Continued)

*Primary Examiner* — Hung T. Nguyen
(74) *Attorney, Agent, or Firm* — Marc A. Began

(57) ABSTRACT

The present invention relates to a medication delivery device comprising a reminder unit for reminding an individual having a medical diseases to take a medicament. The reminder unit comprises means for providing a reminder signal to the individual having the medical disease, the reminder signal being triggered by data associated with a previously occurred event, the associated data being stored in a storage means. Alternatively, the reminder signal may be triggered by a position signal generated by position determining means adapted to determine the position of the medication delivery device.

9 Claims, 2 Drawing Sheets

U.S. PATENT DOCUMENTS

| | | | |
|---|---|---|---|
| 7,158,011 B2 * | 1/2007 | Brue | 340/309.16 |
| 7,269,476 B2 * | 9/2007 | Ratnakar | 700/236 |
| 7,304,913 B2 * | 12/2007 | Niemiec et al. | 368/10 |
| 7,366,675 B1 * | 4/2008 | Walker et al. | 705/2 |
| 7,394,405 B2 * | 7/2008 | Godden | 340/996 |
| 7,397,346 B2 * | 7/2008 | Helal et al. | 340/309.16 |
| 2002/0065685 A1 | 5/2002 | Sasaki et al. | |
| 2002/0080034 A1 * | 6/2002 | Yahalom | 340/573.1 |
| 2002/0147135 A1 | 10/2002 | Schnell | |
| 2004/0008123 A1 * | 1/2004 | Carrender et al. | 340/825.49 |
| 2004/0178199 A1 | 9/2004 | Stroup | |
| 2004/0179430 A1 | 9/2004 | Bahar et al. | |
| 2004/0258012 A1 | 12/2004 | Ishii | |
| 2005/0136903 A1 * | 6/2005 | Kashima et al. | 455/418 |

FOREIGN PATENT DOCUMENTS

| | | |
|---|---|---|
| JP | 2004-350088 | 12/2004 |
| WO | WO 01/47466 | 7/2001 |
| WO | WO 2004/026378 | 4/2004 |
| WO | WO 2004/066182 | 8/2004 |

OTHER PUBLICATIONS

Dey et al, CybreMinder: A Context-Aware System for Supporting Reminders (2000) pp. 172-186.

Roth—Flexible Positioning for Location-Based Services (Jun. 6, 2003) pp. 18-32.

English Abstract of JP 2002-165883 Published Jun. 6, 2002.

* cited by examiner

MEDICATION DELIVERY DEVICE WITH REMINDER UNIT

CROSS-REFERENCE TO RELATED APPLICATIONS

This application is a 35 U.S.C. §371 national stage application of International Patent Application PCT/EP2005/014050 (published as WO 2006/069778), filed Dec. 27, 2005, which claimed priority of European Patent Application 04078558.6, filed Dec. 29, 2004; this application further claims priority under 35 U.S.C. §119 of U.S. Provisional Application 60/648,778, filed Feb. 1, 2005.

FIELD OF THE INVENTION

The present invention relates to a medication delivery device comprising a reminder unit for individuals having medical diseases. In particular the present invention relates to a medication delivery device including a reminder unit to remind its user to take an appropriate type and dose of medicament. The reminder to the user may be a time-related reminder, an activity related reminder or a position related reminder.

BACKGROUND OF THE INVENTION

U.S. Pat. No. 6,650,951 discloses an insulin pump having a reminder feature or forgotten bolus warning for an insulin pump user. The feature discloses in U.S. Pat. No. 6,650,951 in a manual feature in that the user must programme expected mealtimes and a delay period starting at the expected eating time. After the delay period a warning is generated if a bolus is not administered. Such warning may be audible sounds or mechanical vibrations. The expected mealtimes may vary from day to day and/or from week to week. Similarly, the day periods may be programmed independently.

U.S. Pat. No. 6,744,350 discloses a method of operating an insulin pump. The insulin pump is configured to selectively deliver a meal bolus. The method comprises entering into the pump a start time for an interval; entering into the pump an end time for the interval; and generating an alarm signal if a meal bolus is not delivered during the interval.

U.S. Pat. No. 6,744,350 also discloses a pump for delivering insulin to a user. The pump comprises a pump mechanism and a meal-bolus program module. The meal-bolus program module is programmed to control the pump mechanism to deliver a meal bolus. An alarm program module is in data communication with the alarm, a timer, and the meal-bolus program module. The alarm module is programmed to generate an alarm signal when the meal-bolus program module does not control the pump mechanism to deliver a meal bolus within a predetermined period of time.

Thus, the reminder systems provided in U.S. Pat. Nos. 6,650,951 and 6,744,350 both require that the user programs the insulin pump to remind him/her to take the medicament at expected mealtimes. Delay periods may optionally be associated with the expected and pre-programmed mealtimes.

EP 1 008 946 is directed to a mobile user device, such as a personal digital assistant (PDA), a wireless telephone, a car phone, or any other programmable device. The device is equipped with a global positioning system (GPS) receiver and is programmable by the user to alert the user when he/she (along with the device) arrives at a predetermined location, as well as to disclose to the user whatever information or whatever action the user chose to associate with the location. Thus, for example, when the user arrives in the vicinity of the post office, the device automatically alerts him/her that he/she has a letter to post; when the user passes the local grocery store, the device alerts him/her and displays to him/her a shopping list; and when the user arrives at home, the device alerts him/her to check the furnace filters. Consequently, the user does not have to rely on his memory to be reminded of desired information or actions upon his arrival at a particular location.

It is an object of the present invention to provide a medication delivery device including a reminder unit that automatically reminds an individual having a medical disease to take his/hers medicine when a given event occurs. Such an event could be a time-related event, an activity generated event or a position generated event.

SUMMARY OF THE INVENTION

The above-mentioned object is complied with by providing, in a first aspect, a medication delivery device comprising a reminder unit for reminding an individual having a medical disease to take a medicament, the reminder unit comprising
  means for processing a position signal generated by position determining means, and
  means for providing a reminder signal to the individual, the reminder signal being triggered in response to the position signal The reminder signal may be presented as an audible signal, a visible signal, a vibration signal or a combination thereof. The reminder signal may be provided to the individual as a sms or mms message, or as an e-mail. The reminder signal may provide a variety of information to the user. For example, the reminder signal may provide information relating to the amount of medicament to be taken, the sort of medicament to be taken, a time period within which a given medicament should preferably be taken etc. No matter the type of information provided to the user the reminder signal is triggered by the medication delivery device being at a given position. Such position may be the position of a restaurant, a sport facility, a wood etc.

The position determining means or system may comprise a Global Positioning System (GPS) receiver unit. Such position determining means are commercially available with the locations of restaurants, sports facilities etc. already stored therein. Thus, if such systems are applied, the position signal may be generated when the medication delivery device is brought to, for example, a given restaurant. The position signal triggers the reminder signal which reminds the individual to take his/hers medicament for example before eating.

The position determining means may communicate the position signal to the medication delivery device by wireless means, such as for example Bluetooth-based techniques.

The triggering of the reminder signal may also be linked to or associated with a previously occurred event at the position where a position signal is generated. For example, a scenario could be that the last time the individual ate at a given restaurant he/she took an insufficient amount of medicament, such as insulin. The fact that an insufficient amount of medicament was taken has been registered in the reminder unit by the user as an event to be avoided the next time the user wants to eat at the same restaurant. Thus, an alarm is raised so that such negative events can be avoided by adjusting the new dose of medicament to be taken.

The position determining means may also determine the position of the reminder unit and thereby the medication delivery device by other means. Such other means could for example be methods based on triangulations or field strength calculations. Alternatively, the position of the reminder unit/medication delivery device may be determined using a wireless network covering the area in which the reminder unit/ medication delivery device is located. For example MAC addresses of a base unit in such as wireless network could be applied to locate the reminder unit.

The medication delivery device may further comprise an ejection system for providing the medicament, the injection system comprising a piston rod adapted to be driven by an electromagnetic device, such as an electromagnetic motor. Furthermore, the medication delivery device may comprise means, such as a holder, for holding a cartridge containing the medicament.

The position determining means or system may form an integral part of the medication delivery device. Thus, the medication delivery device may have a built-in GPS receiver module with all relevant positions, such as restaurants, sports facilities, stored therein. This list of relevant positions is by no means exhaustive.

In a second aspect, the present invention relates to a medication delivery device comprising a reminder unit for reminding an individual having a medical disease to take a medicament, the reminder unit comprising storage means for storing data associated with a previously occurred event, and means for providing a reminder signal to the individual, the reminder signal being triggered by data associated with a previously occurred event, the associated data being stored in the storage means.

A previously occurred event may be a situation where the individual having the medical disease took an insufficient amount of medicament the last time he or she ate at a given restaurant. Again, the fact that an insufficient amount of medicament was taken has been registered in the reminder unit by the user as an event to be avoided the next time the user wants to eat at the same restaurant. Thus, an alarm is raised so that such negative events can be avoided by adjusting the new dose of medicament to be taken.

Also, previously occurred events may be sport events and the associated data may be data relating to the pulse rate, the blood pressure etc.

In a third aspect, the present invention relates to use of a medication delivery device for reminding an individual having a medical disease to take a medicament, the use comprising the step of providing a reminder signal to the individual, the reminder signal being triggered by a position signal generated by a position determining means adapted to determine the position of the individual. The reminder signal may comprise information relating to the amount of medicament to be taken by the individual at or in the neighbourhood of the position that triggered the reminder signal.

The generated position signal may be a GPS-based position signal. Similarly, the position signal may be provided from the position determining means to the medication delivery device by means of wireless communication, such as Bluetooth wireless communication.

In a fourth aspect, the present invention relates to use of a medication delivery device for reminding an individual having a medical disease to take a medicament, the use comprising the step of providing a reminder signal to the individual, the reminder signal being triggered by data associated with a previously occurred event, the associated data being provided from a storage means. The associated data may be related to events selected from the group consisting of: sleeping, eating, physical activity and time-related events. The associated data may represent the pulse rate or blood pressure of the individual.

In a fifth aspect, the present invention relates to a method for reminding an individual having a medical disease to take a medicament, the method comprising the step of providing a reminder signal to the individual, the reminder signal being triggered by a position signal generated by position determining means adapted to determine the position of the individual. The reminder signal may comprise information relating to the amount of medicament to be taken by the individual at the position that triggered the reminder signal. The position signal may be a GPS-based position signal generated by a GSP receiver unit in the position determining means. The position signal may be provided from the position determining means by means of wireless communication, such as Bluetooth wireless communication.

In a sixth aspect, the present invention relates to a method for reminding an individual having a medical disease to take a medicament, the method comprising the step of providing a reminder signal to the individual, the reminder signal being triggered by data associated with a previously occurred event, the associated data being provided from a storage means.

The previously occurred event may comprise events such as sleeping, eating, physical activity or time-related events. Activity-related events may be events related to sport events or other types of event related to physical exercising.

In a seventh and final aspect, the present invention relates to an insulin pump comprising a reminder unit according to the first and second aspects of the present invention. Also, in the fifth aspect, the present invention relates to an insulin pump comprising a reminder unit capable of performing the methods according to the third and fourth aspects of the present invention.

The generation of the reminders may be controlled and/or generated by software and/or hardware incorporated into the reminder unit. For example, an ASIC with embedded software may form part of the overall control system of the reminder unit. Beside controlling and generating the reminder, the embedded software may also control or administer information or data upon which a reminder is generated. As ready mentioned such data could be data relating to an insufficient amount of medication taken at an earlier stage, or is may be data relating to a previously occurred event, such as a sport event. In case of a sport event, the data could be data relating to the pulse rate of the individual having the medical disease.

To present the reminder to the user, or maybe to a group of users, the reminder unit may be connected to display means, such as a liquid crystal display or another type of flat panel display. As already mentioned, the reminder to the user may also comprise an audible part and/or a mechanical vibration part.

BRIEF DESCRIPTION OF THE DRAWINGS

The present invention will now be explained with reference to a accompanying figures wherein.

Figure 1:
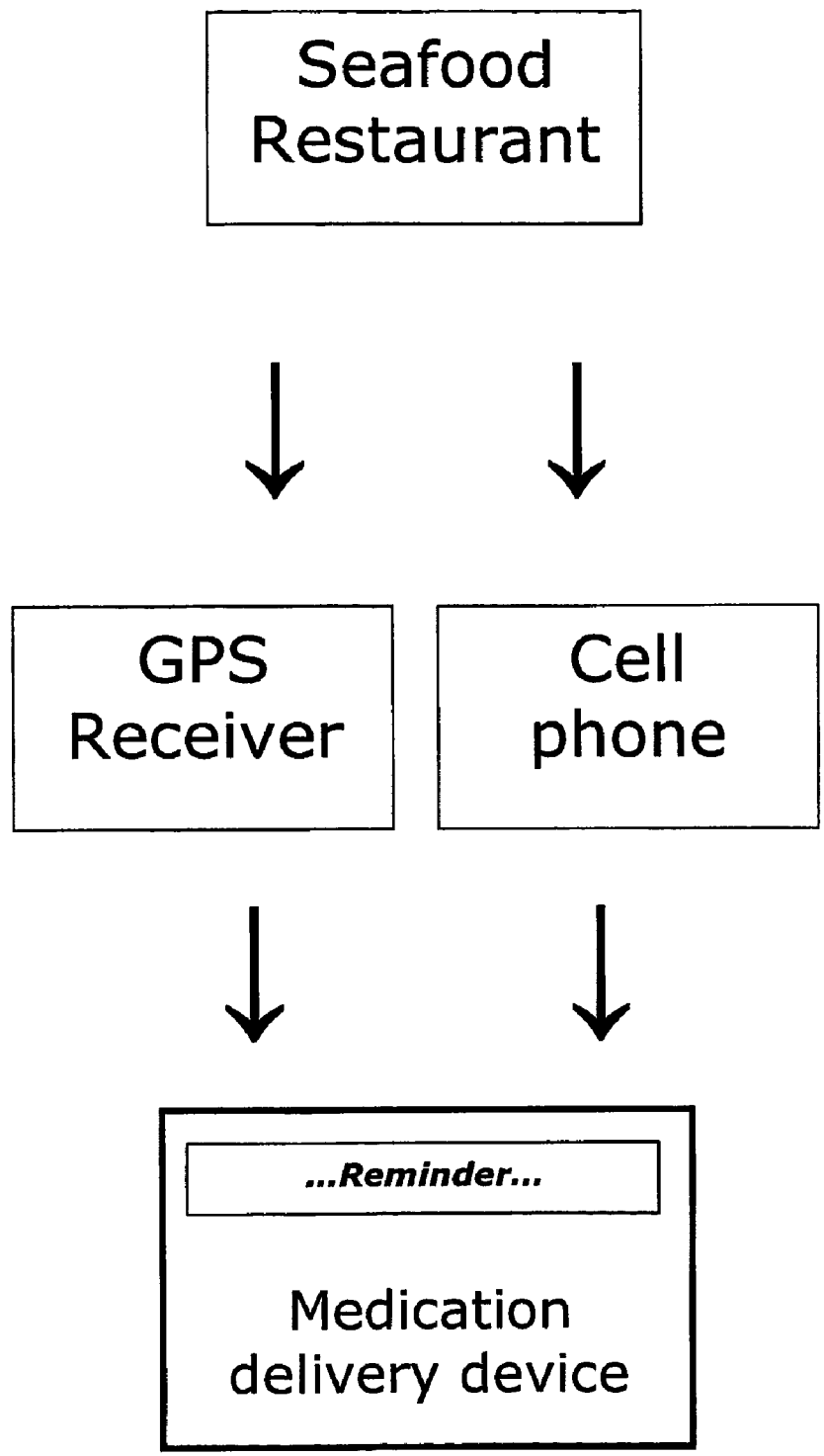
FIG. 1 shows a first embodiment of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

An embodiment of the present invention is depicted in FIG. 1. The reminder unit of the medication delivery device receives a position signal from an external positioning system which can be a cell phone, a GPS receiver module, a GPS navigator unit or any other system capable of determining its own position and communicate the determined position to the reminder unit. One advantage of such commercially available positioning systems is that positions of restaurants, sport facilities etc. are pre-stored in the positioning system. Thus, such commercially available positioning systems are for example capable of relating the name of a restaurant to a coordinate, such as 56° 08' 15" N 10° 13'00" E.

The positioning system is used to generate a position signal to the reminder unit when the reminder unit, and thereby also the medication delivery device, is at a given position, such as the position of given restaurant. In the embodiment depicted in FIG. 1 the external positioning system communicates with the reminder unit using a wireless link, such as a Bluetooth link.

In its most general aspect the reminder unit of the medication delivery device generates a reminder signal in response to a position signal generated by the positioning system. The position signal is triggered in response to the detection of a given position of the reminder unit. As illustrated in FIG. 1 this given position can be the position of a sport facility or a restaurant—the latter here being exemplified as a Seafood restaurant. In the case of the Seafood restaurant, a user having a medical disease is prompted to take his/her medicament in case he/she wants to eat at the Seafood restaurant because the position, and thereby the coordinates of that particular Seafood restaurant, is known to and pre-stored in the positioning system.

Besides being generated in response to a position signal only, other types of data may also influence the generation of the reminder signal. For example, pre-stored information in terms of data entered into the system by the user and relating to a previously occurred event may be decisive in terms of whether a reminder signal is generated or not. Such pre-stored data could be that the individual having the medical disease took an insufficient amount of medicament the last time he or she ate at a given restaurant. The fact that an insufficient amount of medicament was taken has been registered in the reminder unit by the user as an event to be avoided the next time the user wants to eat at the same restaurant. Thus, an alarm in form of a reminder signal is raised so that such events can be avoided.

Figure 2:
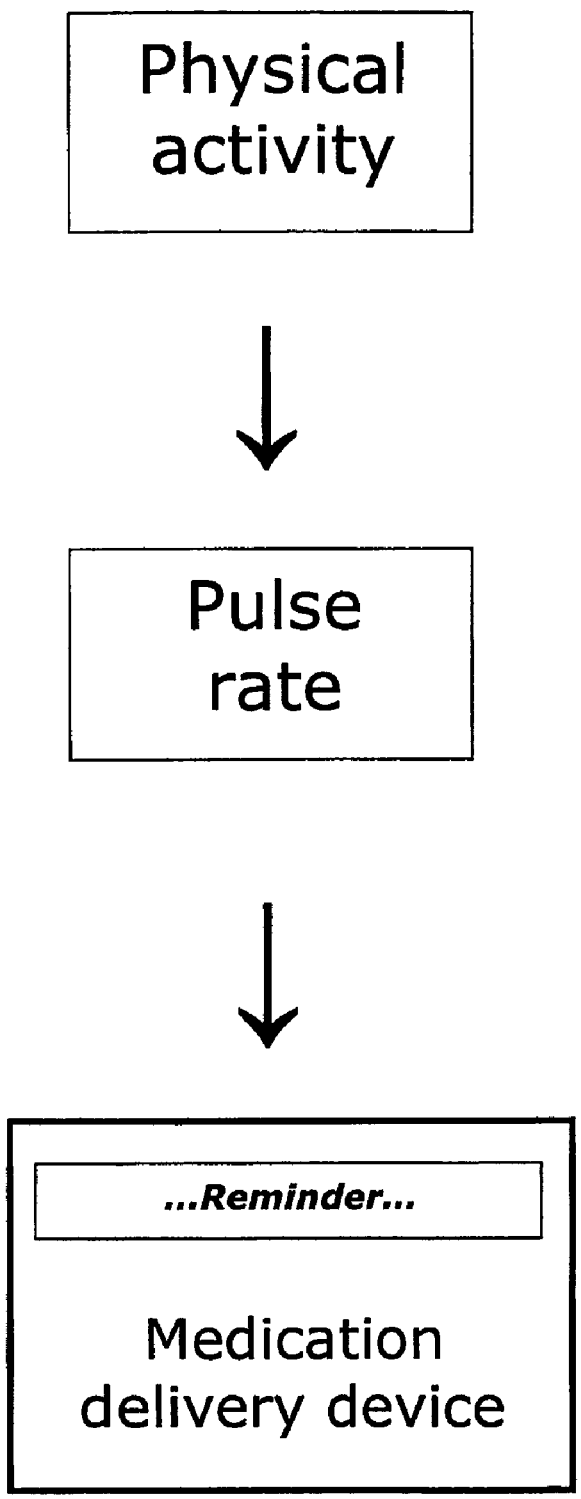
FIG. 2 shows a second embodiment of the present invention.

In another embodiment of the present invention reminder signals are triggered by certain types of activity—see FIG. 2. For example, monitoring the pulse rate of a person reveals whether the person is at rest or performs some kind of physical activity, such as jogging, swimming etc. This activity-related monitoring is also capable of triggering a reminder signal. Again, pre-stored data or information entered into the system by the user and relating to a previously occurred event may influence whether a reminder signal is generated or not.

Such pre-stored data or information could be that the individual having the medical disease took an insufficient amount of medicament the last time he/she had a pulse rate above a certain level. The fact that an insufficient amount of medicament was taken has been registered in the reminder unit by the user as an event to be avoided in the future.

The invention claimed is:

1. A medication delivery device comprising a reminder unit for reminding an individual having a medical disease to take a medicament, the reminder unit comprising
    means for processing a position signal generated by position determining means, and
    means for providing a reminder signal to the individual, the reminder signal being triggered in response to the position signal, and
    wherein the means for processing the position further comprises a means for comparing the position of the medication delivery device to the proximity to an eating establishment and wherein the reminder signal is generated when the device is near the eating establishment and wherein the reminder signal is a reminder signal associated with taking diabetes medication.

2. A medication delivery device according to claim 1, wherein the reminder unit comprises means for providing the reminder signal as an audible signal, a visible signal, or a vibration signal or any combination thereof.

3. A medication delivery device according to claim 1, wherein the reminder signal comprises information relating to an amount of medicament to be taken by the individual.

4. A medication delivery device according to claim 1, further comprising an ejection system for assisting expelling the medicament, the injection system comprising a piston rod adapted to be driven by an electromagnetic device, such as an electromagnetic motor.

5. A medication delivery device according to claim 1, further comprising means for holding a cartridge containing the medicament.

6. A medication delivery device according to claim 1, wherein the position determining means forms an integral part of the medication delivery device.

7. A medication delivery device according to claim 1, wherein the position determining means comprises a GPS receiver unit.

8. A medication delivery device according to claim 1, wherein the position determining means is adapted to apply triangulations or field strength calculations to determine the position of the medication delivery device.

9. A medication delivery device according to claim 1, wherein the position determining means is adapted to apply a MAC address of a base unit in a wireless network to determine the position of the medication delivery device.

* * * * *